(12) United States Patent
Delfino

(10) Patent No.: US 6,676,595 B1
(45) Date of Patent: Jan. 13, 2004

(54) RADIOACTIVE MEDICAL IMPLANT AND METHOD OF MANUFACTURING

(75) Inventor: Michelangelo Delfino, Los Altos, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/379,819

(22) Filed: Aug. 24, 1999

(Under 37 CFR 1.47)

Related U.S. Application Data
(60) Provisional application No. 60/097,563, filed on Aug. 24, 1998.

(51) Int. Cl.[7] .................................................. A61F 2/02
(52) U.S. Cl. ......................................................... 600/30
(58) Field of Search ................................ 600/1, 2, 3, 4, 600/5, 6, 7, 8; 424/1.29, 422, 1.65, 9.36, 1.61; 623/11.11, 18.11, 22.11, 23.11

(56) References Cited

U.S. PATENT DOCUMENTS

| | | |
|---|---|---|
| 4,421,988 A | 12/1983 | Robertson et al. |
| 4,433,247 A | 2/1984 | Turner |
| 4,764,394 A | 8/1988 | Conrad |
| 5,342,283 A | 8/1994 | Good |
| 5,711,812 A | 1/1998 | Chapek et al. |
| 6,060,036 A * | 5/2000 | Armini .......................... 600/3 |
| 6,120,540 A * | 9/2000 | Apple et al. ............. 623/11.11 |
| 6,183,409 B1 * | 2/2001 | Armini .......................... 600/3 |

OTHER PUBLICATIONS

Hehrlein et al., "Pure β–Particle–Emitting Stents Inhibit Neointima Formation in Rabbits," 93 *Circulation* (4), pp. 641–645 (Feb. 15, 1996).

* cited by examiner

Primary Examiner—Max F. Hindenburg
Assistant Examiner—Brian Szmal
(74) Attorney, Agent, or Firm—Baker & McKenzie

(57) ABSTRACT

A medical implant for use in brachytherapy or other medical treatment preferably having a silicon base and radioactive ions implanted in it. Preferably radioactive xenon ions are used. An ion implantation process is provided for doping the silicon substrate with the radioactive ions in a controlled fashion.

20 Claims, 1 Drawing Sheet

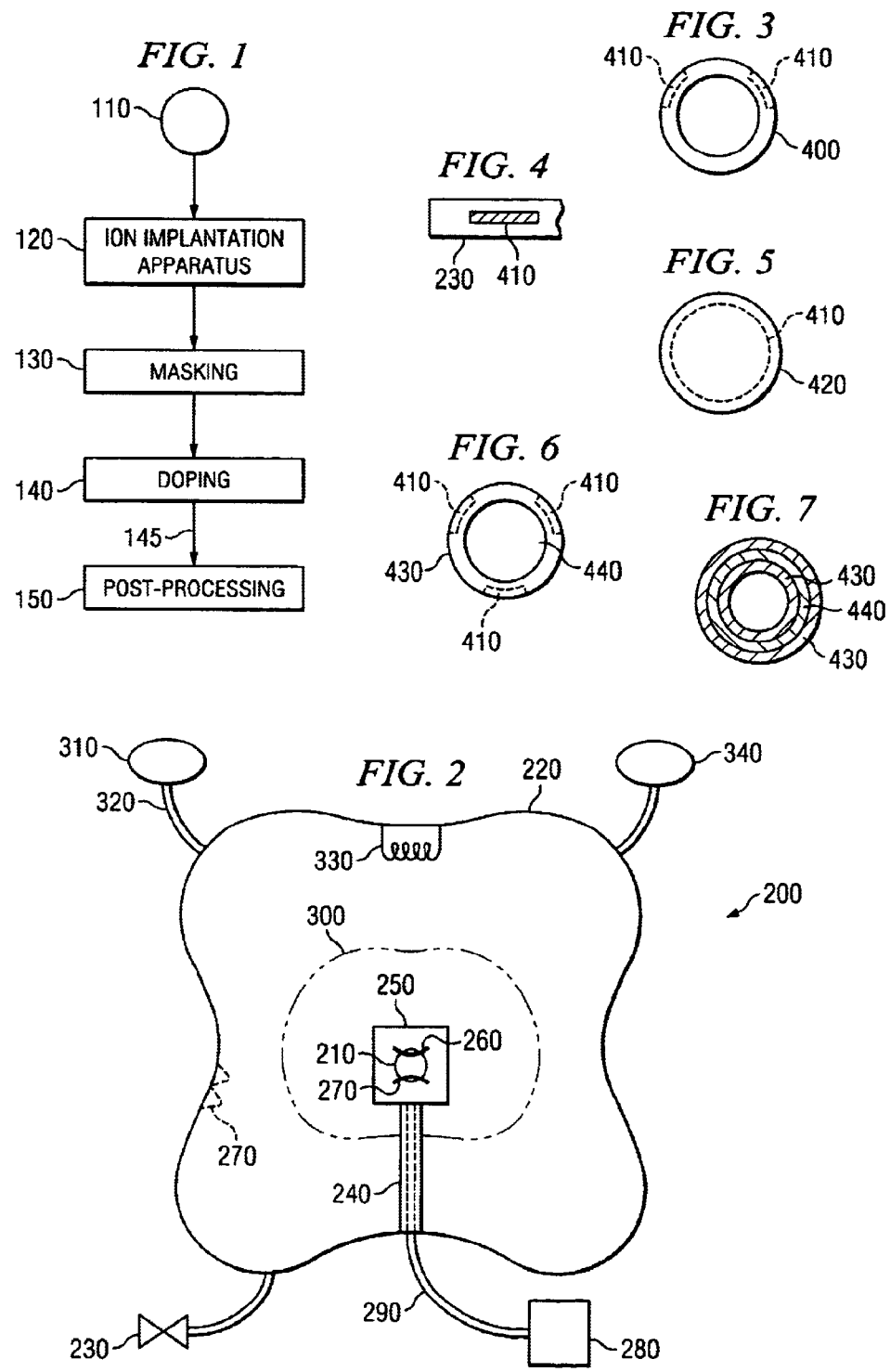

RADIOACTIVE MEDICAL IMPLANT AND METHOD OF MANUFACTURING

Priority is claimed from Provisional Application Serial No. 60/097,563, filed Aug. 24, 1998, entitled "Radioactive Medical Implant and Method of Manufacturing."

FIELD OF THE INVENTION

The present invention relates to a radioactive implant, such as a seed for use in brachytherapy, and to a method for imparting radioactive properties to an implant substrate.

BACKGROUND OF THE INVENTION

Radiation therapy has long been used to treat cancer and other diseases of the body. It is understood that the targeted application of radiation destroys the cells in the targeted area, such as rapidly multiplying cells, i.e., cancerous cells, thereby providing a disease therapy. One form of radiation therapy is brachytherapy, which generally provides a targeted application of a relatively short half-life radiation source. The radiation source, typically called a brachytherapy seed or implant, is implanted in a specific area to be treated, such as directly at an identified tumor location. Depending on factors such as the size and shape of the tumor and the type of treatment desired, the radioactive source is kept either permanently in the body or removed after a period of time.

Various forms of implants are known for use in brachytherapy, such as radium needles, ribbons and capsules. Multi-layered implants are also known in which a radioactive layer is coated upon a substrate. Examples of such multi-layered implants are discussed in Good, U.S. Pat. No. 5,342,283. In such multi-layered implants it is known to provide a substrate, such as a microsphere, ribbon or fabric and then to form a radioactive layer on the substrate using various methods such as plating techniques including sputtering, cathode arc plasma deposition, laser ablation of the target material in the presence of a radioactive gas or reaction of an excited radionuclide gas with a target material. A disadvantage of such techniques is difficulty in achieving a combination of high ion fluence at a relatively high ion energy to achieve a high concentration of a radioactive isotope such as xenon or another radioactive isotope of an inert gas, such as argon, krypton, or radon. Other known techniques involve very high temperatures above the melting points of the materials being used to manufacture the implants.

Ion implantation is a known methodology for introducing dopant atoms into a silicon substrate, such as in semiconductor chip manufacturing. Generally speaking, ions are directed with varying degrees of acceleration towards the silicon semiconductor substrate. The ions are accelerated by a high voltage differential created between the ion source and the semiconductor substrate (or a cathode adjacent the substrate). The ions are introduced into the substrate by virtue of the momentum of the ions causing them to become embedded within the crystalline lattice of the semiconductor substrate. The implanted ions are understood to cause interference with the lattice structure by being implanted in a random fashion. Annealing is typically used to restore the lattice structure and allow the implanted atoms to migrate to occupy lattice sites. Examples of ion implantation techniques and apparatus can be found, for example, in commonly assigned U.S. Pat. Nos. 4,421,988, 4,433,247, and 5,711,812.

For medical applications, inert gases provide desirable sources of radioactive ions. However, known methods and apparatus for creating radioactive medical implants do not provide an economical or efficient technique for implanting an inert gas in a substrate. Although sputtering has been proposed, the sputtering process works at lower energies and does not result in an efficient incorporation of gas ions into the substrate.

From the above, it is apparent that there is a need for an improved system to manufacture radioactive medical implants such as stents or brachytherapy seeds. It is accordingly an objective of the present invention to provide a system and method using ion implantation for effectively making stents, brachytherapy seeds or other medical implants having a radioactive isotope implanted in a substrate and preferably providing effective control of the radioactive dosage imparted.

It is a further object of the present invention to provide a system and method of achieving high concentrations of a radioactive isotope of an inert gas, such as xenon-133 in a medical implant.

In order to achieve a medical implant that does not readily degrade in use, it is a further objective of the present invention to provide a system and method for implanting a radioactive isotope below the surface of a medical implant substrate.

It is another object of the invention to provide a medical implant having a determined amount of a radioactive ion implanted in its outer crystalline lattice.

It is a further object of the present invention to improve the dosage and uniformity of the radioactive layer used in radioactive implant production.

It is another object of the present invention to provide an improved method of making radioactive implants from a medical substrate, such as silicon, having a thermally stable radioactive layer and a high concentration of ions.

A still further object of the present invention is to provide a method of preparing a radioactive implant with the ability to implant ions in a closed vacuum system, which allows for efficient disposal of any excess radionuclide into a storage cylinder for disposal after sufficient decay has occurred.

Another object of the present invention is to provide a method of making a radioactive implant and for manufacturing a radioactive implant, allowing for increased accuracy in determination of the radioactive dose control, and achieving a greater degree of dosage uniformity.

SUMMARY OF THE INVENTION

The present invention alleviates to a great extent the disadvantages of the known structures and systems for manufacturing radioactive implants and achieves the objects noted above, by providing an apparatus and method of doping a silicon based substrate material with a radioactive ion, thereby implanting the ion within the substrate material. An ion implantation doping technique is used to bombard the silicon based substrate with a radioactive ion, preferably xenon-133, or other inert gas such as argon, krypton or radon. The radioactive dosage is controlled by controlling various bombardment parameters including time, voltage and the amount of the surface area of the substrate material targeted. A preferred implant has a radioactive xenon ion implanted in a silicon matrix.

In one embodiment, a silicon substrate is a pre-formed implant such as a stent or other shape, or alternatively may be a substrate material that is suitable for later formation into a useful device. The substrate material preferably is silicon and may be of any form, such as amorphous or crystalline.

In one example, the substrate material is preformed into a medical stent. In another embodiment, a thin layer of silicon may be formed over another appropriate base material. The application of the present invention is not limited to particular shapes or sizes of devices irradiated.

Any technique of ion implantation may be used to form the radioactive layer. In one embodiment, a closed vacuum system is used, in which one takes the steps of pumping a leak-tight vacuum chamber to a low base pressure; introducing xenon-133 gas to a few millitorr; igniting a plasma; creating a sufficient voltage differential to accelerate the ions to the target silicon substrate material; extinguishing the plasma when the desired dose is achieved and pumping out the excess xenon-133 into a storage cylinder for disposal after sufficient decay has occurred. A doped radioactive region is formed on the surface of the implant at various energy levels, such as between 1 and 200 keV, and corresponding ion fluences between $6.5 \times 10^{15}$ and $5.7 \times 10^{16}/cm^2$, although any ion implantation energy and ion fluence that can achieve a sufficient amount of doping may be used. These preferred ion implantation energies and ion fluences can achieve an average concentration of 10 atomic percent xenon-133 at the surface of the substrate material. The implant may be post-annealed at high temperature to provide a thermally stable xenon-133 atom-silicon atom couple. Typically, the radioactive ions are implanted on all the exposed surfaces of the substrate, although specific regions of the substrate may be selected, such as by using masking.

One advantage of the present invention is the ability to independently control ion-fluence, ion-impingement rates and the ion-energy in the ion implantation process, thus providing control of the concentration of radionuclide into the substrate or target. Another advantage of the invention is the ability to implant ions in a closed vacuum system in a controlled way, thereby minimizing handling problems associated with disposal of radioactive materials.

It is a further advantage of the present invention that a system and method of achieving high concentrations of a radioactive isotope of an inert gas, such as xenon-133 in a medical implant is provided.

Another advantage of the present invention is that a medical implant is achieved that does not readily degrade in use because the radioactive isotope is implanted below the surface of a medical implant substrate.

BRIEF DESCRIPTION OF THE DRAWINGS

The above and other objects and advantages of the invention will be apparent upon consideration of the following detailed description, taken in conjunction with the accompanying drawings in which like reference characters refer to like parts throughout, and in which:

FIG. 1 is an illustration of ion implantation processing and apparatus in accordance with the present invention;

FIG. 2 is an illustration of an ion implantation apparatus in accordance with the present invention;

FIG. 3 is a cross-section of a doped substrate material in accordance with the present invention;

FIG. 4 is a plan view of another embodiment of the doped substrate material in accordance with the present invention;

FIG. 5 is a cross-section of another embodiment of the doped substrate material in accordance with the present invention;

FIG. 6 is a cross-section of a multi-layer doped substrate material embodiment in accordance with the present invention; and FIG. 7 is a cross-section of a multi-layer substrate material including ion receiving layers, in accordance with the present invention.

DETAILED DESCRIPTION OF THE INVENTION

In accordance with the present invention, a radioactive material or a radioactive medical device such as an implant for in vivo implantation is generally created by doping a suitable substrate, such as silicon, by bombarding the substrate with ions of a suitable material, such as xenon-133 or other inert gas, such as argon, krypton or radon (such as radon-222), so the ions become implanted within the substrate. In this description, each of "substrate" and "substrate material" will be used to refer to the material receiving the implanted radioactive isotope.

In the illustrated embodiment, the substrate material is pre-formed into a desired useful shape, such as a brachytherapy implant, stent, filament, wire, plate, microsphere or other shape. This step is diagrammatically indicated by reference numeral 110 in FIG. 1 and is optional in that the substrate material may be doped prior to formation into the desired shape. It is preferred to pre-form the substrate to avoid necessitating further handling of the doped material following ion implantation. Any structure of the substrate material 210 (FIG. 2) prior to doping may be used, so long as it is compatible with the ion implantation apparatus used.

It is preferred that the substrate material 210 be an amorphous or crystalline form of silicon or metal silicide, which is suitable for in vivo implantation, such as in a tumor or body lumen. Alternatively, a silicon layer for doping may be deposited on any other material capable of receiving and retaining the silicon. Such other materials may include metallic materials, non-metallic materials, ceramics, composites of metallic and non-metallic materials or other composites. It is also desirable that both the radioactive isotope and the substrate material be thermally stable so that during processing and post-annealing or heat treatment, little of the implanted radioactive ion, such as xenon-133, is lost.

In the doping process, the pre-formed substrate is placed within the ion implantation apparatus. The placement of the pre-formed substrate in the ion implantation apparatus is illustrated with box 120 in FIG. 1. The ion implantation apparatus is indicated with reference number 200 in FIG. 2. Any form of ion implantation apparatus 200 may be used that can receive the substrate material 210 and introduce the radioactive ion, such as xenon-133, at sufficient energies. Likewise any number of substrate materials to be doped may be placed within the ion implantation apparatus. For example, a single item may be doped or plural items may be doped together. In the illustrated embodiment, a target area for doping is then selected, although targeting is optional. Targeting a particular area on the substrate for doping, if desired, may be done by any technique. For example, the ion beam may be directed at a particular region of the substrate. Likewise, masking may be used, to make a doping pattern determined by the mask pattern. In the illustrated embodiment masking is used, as indicated by reference numeral 130.

Following target area selection, the doping process is preferably undertaken, indicated with reference numeral 140. As discussed previously, any ion implantation apparatus or technique may be used to perform this operation. By way of example, plasma doping (PLAD) can be used under certain circumstances.

The ion implantation apparatus 200 includes a leak-tight chamber 220. A vacuum pump 230 is connected to the interior of the chamber 220 and operates to evacuate the chamber 220 to a relatively low base pressure vacuum level, for example, on the order of $10^{-6}$ torr. A substrate material 210 is placed substantially in the interior of the chamber on a support 240. The support 240 is preferably a part of an electrode 250, or includes an electrode 250. For the purpose of illustration only, the electrode is denoted with reference numeral 250, although it should be understood that any placement or formation of the electrode 250 may be used such that the electrode 250 can become electrically charged. Optionally, the support 240 and/or electrode 250 may include retaining elements 260 retaining the substrate material 210 in place during processing. The substrate material 210 may be placed on the support 240 through an aperture in the chamber 220, which includes a sealing element 270. Alternatively, the support 240 may be movable and the substrate material 210 may be placed on the support outside the chamber 220 and then the support 240 and substrate material 210 may be moved together into position within the chamber 220. Preferably the sealing element 270, seals the aperture in an air-tight fashion. The substrate material 210 may be placed on the support 240 by any means, such as manually, using a robotic arm or gripper or other conveyor. The retaining elements 260 preferably hold the substrate material 210 in a fixed position and serve to ensure that there is an electrical contact between the substrate material 210 and the electrode 250. A high voltage, pulse power supply 280 is used to provide high voltage through a supply line 290 to the electrode 250. Optionally, the support 240 is conductive and the supply line 290 supplies an electrical connection via the support 240. The supply provides repetitive pulses of high voltage in the 1 to 200 kV range. It should be appreciated that this description of the ion implantation apparatus 200 is for illustration only and that any ion implantation apparatus may be used. In addition, other energy levels can be used.

An ionized plasma 300 is created that surrounds the substrate material 210 within the chamber so that ions may be accelerated into the substrate material 210 from all sides. To sustain the surrounding plasma, a gas source 310 is connected by a conduit 320 to introduce ionizing radioactive gas at a low, controlled rate into the chamber after it is evacuated by the vacuum pump. Any suitable operating pressure within the chamber may be used, such as a pressure on the order of $10^{-3}$ torr. Therefore, prior to ionization, there will be a low pressure atmosphere of the radioactive gas from the gas source within the chamber 220. The radioactive gas within the chamber 220 may be ionized in various ways. For example, a beam of electrons from a heated filament 330 may be directed into the interior of the chamber 220 to collide with the radioactive gas to form ions. It is readily apparent that various other sources of ionizing radiation such as radio frequency electromagnetic radiation may be utilized to ionize the gas within the chamber to form the plasma 300 that surrounds the substrate material 210. Optionally, the areas of the substrate material 210 that are bombarded with the accelerated ions may be specified by masking.

The plasma igniting pulse may be provided simultaneously with the accelerating pulse. In such a system, heated filament 330 is not required. Rather, the plasma igniting pulse is provided by electrode 250 simultaneously with an accelerating pulse. In this embodiment, a voltage pulse is supplied, thereby creating a plasma 300 adjacent the substrate 210 object and accelerating and implanting ions from the plasma into the substrate 210.

Preferably a number of pulses of a high voltage in the 1 to 200 kV range are applied to the electrode 250 to accelerate the ions in the plasma 300 toward the substrate material 210 at an ion energy sufficient to implant ions into the substrate material 210. The number of pulses applied varies depending on the dose of ions to be implanted in the substrate material 210. After a predetermined dose of ions has been implanted in the substrate material 210, the application of high voltage pulses to the radioactive gas is discontinued thereby extinguishing the plasma.

In an embodiment of the invention where the substrate material 210 is silicon and the radioactive gas is xenon-133, the xenon-133 ions are preferably accelerated to impact the silicon substrate material at an energy sufficient to drive ions on average at least 10 nanometers beneath the surface of the silicon. Under typical conditions, this depth of xenon-133 ion penetration may be obtained by accelerating the ions toward the silicon substrate material at an average energy of at least 10 keV. It is also preferred that the dose of xenon-133 ions implanted in the silicon substrate be in the range from about $6.5 \times 10^{15}$ to about $5.7 \times 10^{16}$ ions per square centimeter, although any suitable dosage may be achieved. A depth distribution of implanted ions is achieved. In other words, although the mean depth of the implanted ions may be at a particular level, ions are distributed at depths varying from the mean. One exemplary ion depth distribution is illustrated in Table 1 below. As seen in Table 1, a generally Gaussian depth distribution can be achieved at which the mean depth is indicated by $R_p$, dimensioned in micrometers ($\mu$m). The majority of ions (approximately 68%) in such a distribution are within a distribution range ($\Delta R_p$) from the mean depth of $R_p$.

TABLE 1

| E (keV) | $R_p$ ($\mu$m) | $\Delta R_p$ ($\mu$m) | $R_p + 3 \Delta R_p$ ($\mu$m) |
|---------|----------------|------------------------|-------------------------------|
| 10      | 0.0087         | 0.0014                 | 0.0129                        |
| 20      | 0.0139         | 0.0022                 | 0.0205                        |
| 30      | 0.0184         | 0.0029                 | 0.0271                        |
| 50      | 0.0266         | 0.0042                 | 0.0392                        |
| 100     | 0.0448         | 0.0068                 | 0.0652                        |
| 200     | 0.0785         | 0.0115                 | 0.1130                        |

As illustrated in Table 1, the majority of the implanted ions are beneath the surface of the substrate, diminishing degradation during use and making implantation using the techniques described here particularly well suited for use in medical applications. The depth distribution of between 99% and 100% of the implanted ions is indicated in the last column ($R_p + 3 \Delta R_p$). As seen in Table 1, almost all of the implanted xenon ions at an energy level of 50 keV are in a band of plus or minus 0.0392 $\mu$m from the mean depth of 0.0266 $\mu$m. It is also seen that at energy levels between 10 keV and 200 keV, the mean depth of the implanted ions is between approximately 0.0080 $\mu$m and 0.08 $\mu$m.

Any radioactive gas remaining in the chamber 220 after the plasma is extinguished is preferably evacuated into a storage container 340. The radioactive gas in the storage container 340 preferably is subsequently allowed to decay to a safe level of radioactivity before disposal. The now doped and radioactive substrate material 210 may be removed at any time following processing, by any means. Following processing, the doped substrate material 210 may be subjected to post-processing, as indicated by reference number 150 in FIG. 1.

It is generally noted that if the substrate material 210 has a crystalline surface layer before application of the ion implantation or doping process 140, the surface layer may be converted to an amorphous layer during the process. In this case, the substrate material may be annealed during post-processing 150 in order to recrystallize a surface layer of the substrate material 210. Anneal temperatures of 450° C. to 900° C. are preferred. At 450° C., anneal times exceeding 30 minutes are preferred. At 900° C. or higher, anneal times of approximately 10 minutes or less are possible. Preferably the annealing process is performed in a non-oxidizing atmosphere such as hydrogen, nitrogen, argon or mixtures thereof.

Radioactive ions, such as xenon-133, are extracted from a plasma source and accelerated to a predetermined energy level and then directed into a surface of the substrate material to uniformly implant ions on the surface of the substrate material 210. The substrate material optionally may be manipulated during processing to expose desired areas of the substrate material 210 to be exposed to the path of the ion beam. In that way, the exposed areas are bombarded with the ions and thereby a doping region is created.

As discussed previously, the substrate material 210 may be preformed into any shape prior to processing. In one embodiment, a medical stent is provided. By way of example, a generally tubular stent is illustrated in FIG. 3, although it is understood that any form of stent, such as a filament or latticed stent may be used. As illustrated in FIG. 3, the stent 400 has doping regions in which the radioactive ion, such as xenon-133 has been doped into the stent material. In the illustrated embodiment, two doping regions 410 are shown. Other doping profiles may be selected. For example, the doping layer may alternatively cover the entire outer surface of the stent.

Another example is illustrated in FIG. 4. In this example, the substrate material 210 is a filament and is illustrated in plan view. As illustrated, a discrete doping region 410 is illustrated, although alternatively the entire surface of the filament or plural regions may be doped.

Any shape of brachytherapy seed may also be created. In one embodiment, a sphere 420, as illustrated in FIG. 6 may be used. Preferably, the substrate material used for the sphere 420 is a silicon material. The illustrated doping layer 410 covers the entire surface of the sphere 420 and is created by implanting xenon-133 in the substrate. One form of brachytherapy sphere is a microsphere, such as having a 400–800 μm diameter although other size spheres also may be used.

The silicon is doped with xenon-133 at energies preferably between 10 and 200 keV, and corresponding ion fluences between $6.5 \times 10^{15}/cm^2$ and $5.7 \times 10^{16}/cm^2$ to give an average concentration of 10 atomic percent xenon-133 at the surface of the doped sphere 420. The sphere 420 optionally is post-annealed at high temperature to recrystallize the surface layer of the sphere 420 and to provide a thermally stable xenon-133 atom-silicon atom couple.

In another embodiment a silicon layer 430 for doping is coated on another material 440 capable of receiving and retaining the silicon, as illustrated in FIG. 7. Silicon layers 430 may be formed on particular areas of the material 440, or alternatively, may coat all exposed surfaces, as illustrated in FIG. 6. Such other materials 440 may include metallic materials (such as $TiSi_2$, $NiSi_2$), non-metallic materials, ceramics, composites of metallic and non-metallic materials or other composites.

Thus, it is seen that a method for efficiently producing radioactive medical implants, including brachytherapy seeds and stents is provided. One skilled in the art will appreciate that the present invention can be practiced by other than the preferred embodiments, which are presented in this description for purposes of illustration and not of limitation, and the present invention is limited only by the claims that follow.

It is noted that equivalents for the particular embodiments discussed in this description may practice the invention as well.

What is claimed is:

1. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive ions of elements selected from a group consisting of argon, krypton, and radon.

2. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive xenon-133.

3. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive radon-222.

4. A radioactive implant as set forth in claim 1 wherein the substrate material includes silicon.

5. A radioactive implant as set forth in claim 1 wherein the substrate material is selected from the group including of amorphous silicon and crystalline silicon.

6. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive xenon-133 and the substrate material is selected from the group consisting of amorphous silicon and crystalline silicon.

7. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive xenon-133 and the radioactive region of the radioactive implant has a concentration of about 10 atomic percent of the radioactive ion.

8. A radioactive medical implant comprising:
a substrate material having a molecular structure; and
a radioactive surface region in the substrate material including a plurality of radioactive ions incorporated in the molecular structure of the substrate material in the radioactive region, wherein said radioactive ions include radioactive xenon-133 ion that is implanted in the substrate material and has a density in the substrate material in a range from about $6.5 \times 10^{15}$ ions per square centimeter to about $5.7 \times 10^{16}$ ions per square centimeter.

9. The radioactive implant of claim 1 wherein the substrate material is in the form of a medical stent.

10. The radioactive implant of claim 1 wherein the substrate material is in the form of a sphere.

11. The radioactive implant of claim 1 further comprising a core, the substrate material surrounding the core.

12. A radioactive medical implant comprising:

a substrate material having a molecular structure; and a radioactive surface region in the substrate material including a plurality of radioactive ions incorporated in the molecular structure of the substrate material in the radioactive region, wherein, the substrate material is selected from the group consisting of amorphous silicon and crystalline silicon;

the radioactive ion is radioactive xenon-133; and the radioactive ion has a density in the substrate material in a range from about $6.5 \times 10^{15}$ ions per square centimeter to about $5.7 \times 10^{16}$ ions per square centimeter.

13. The radioactive implant of claim 12 wherein over 90% of said radioactive ions are implanted beneath the surface of said substrate.

14. The radioactive implant of claim 12 wherein the mean depth of said radioactive ions at implantation energy levels between 10 keV and 200 keV, the mean depth of the implanted ions is between approximately 0.0080 µm and 0.08 µm.

15. The radioactive implant of claim 12 further comprising a spherical core, the substrate material surrounding the core.

16. A radioactive medical implant comprising:

a substrate material having a surface and a molecular structure wherein the substrate material includes silicon; and a radioactive region in the substrate material including a plurality of radioactive ions are incorporated in the molecular structure of the substrate material in the radioactive region wherein said radioactive ions include radioactive ions of elements selected from a group consisting of argon, krypton, and radon.

17. A radioactive implant as set forth in claim 16 wherein the substrate material is selected from the group including of amorphous silicon and crystalline silicon.

18. The radioactive implant of claim 16 wherein the substrate material is in the form of a medical stent.

19. The radioactive implant of claim 16 wherein the substrate material is in the form of a sphere.

20. The radioactive implant of claim 16 further comprising a core, the substrate material surrounding the core.

* * * * *